United States Patent
Tajdaran et al.

(10) Patent No.: US 11,376,224 B2
(45) Date of Patent: Jul. 5, 2022

(54) SYSTEM FOR DELIVERY OF FK506 FOR ENHANCING NERVE REGENERATION

(71) Applicant: THE HOSPITAL FOR SICK CHILDREN, Toronto (CA)

(72) Inventors: Kasra Tajdaran, North York (CA); Gregory Borschel, Toronto (CA); Tessa Gordon, North York (CA)

(73) Assignee: THE HOSPITAL FOR SICK CHILDREN, Toronto (CA)

( * ) Notice: Subject to any disclaimer, the term of this patent is extended or adjusted under 35 U.S.C. 154(b) by 0 days.

(21) Appl. No.: 16/091,153

(22) PCT Filed: Apr. 4, 2017

(86) PCT No.: PCT/CA2017/050410
§ 371 (c)(1),
(2) Date: Oct. 4, 2018

(87) PCT Pub. No.: WO2017/173534
PCT Pub. Date: Oct. 12, 2017

(65) Prior Publication Data
US 2019/0125688 A1  May 2, 2019

Related U.S. Application Data

(60) Provisional application No. 62/318,500, filed on Apr. 5, 2016.

(51) Int. Cl.
| | |
|---|---|
| *A61K 9/50* | (2006.01) |
| *A61K 9/70* | (2006.01) |
| *A61K 9/00* | (2006.01) |
| *A61K 9/14* | (2006.01) |
| *A61K 47/42* | (2017.01) |
| *A61K 9/06* | (2006.01) |
| *A61K 9/16* | (2006.01) |
| *A61K 47/38* | (2006.01) |
| *A61K 31/453* | (2006.01) |
| *A61K 31/436* | (2006.01) |

(52) U.S. Cl.
CPC .......... *A61K 9/5052* (2013.01); *A61K 9/0085* (2013.01); *A61K 9/06* (2013.01); *A61K 9/14* (2013.01); *A61K 9/1647* (2013.01); *A61K 9/5031* (2013.01); *A61K 9/5089* (2013.01); *A61K 9/7007* (2013.01); *A61K 31/436* (2013.01); *A61K 31/453* (2013.01); *A61K 47/38* (2013.01); *A61K 47/42* (2013.01)

(58) Field of Classification Search
CPC .. A61K 9/5052; A61K 9/7007; A61K 9/0085; A61K 9/14; A61K 47/42; A61K 9/06; A61K 9/1647; A61K 47/38; A61K 9/5031; A61K 31/453; A61K 31/436; A61K 9/5031; A61K 9/5089
See application file for complete search history.

(56) References Cited

U.S. PATENT DOCUMENTS

| | | | | |
|---|---|---|---|---|
| 9,011,921 B2 * | 4/2015 | Lee | ...................... | A61K 31/554 424/489 |
| 2004/0018228 A1 * | 1/2004 | Fischell | ................. | A61K 9/127 424/450 |
| 2006/0153815 A1 * | 7/2006 | Seyda | ................... | C12N 5/0068 424/93.7 |
| 2008/0114469 A1 * | 5/2008 | O'Brien | ................ | A61F 2/0063 623/23.76 |
| 2009/0155326 A1 * | 6/2009 | Mack | ................. | A61K 31/7052 424/402 |

OTHER PUBLICATIONS

Kasra Tajdaran, et al., A Novel Polymeric Drug Delivery System for Localized and Sustained Release of Tacrolimus (FK506), 112 Biotech. Bioeng. 1948 (Year: 2015).*
D. Grinsell & C.P. Keating, Peripheral Nerve Reconstruction After Injury: A Review of Clinical and Experimental Therapies, 2014 Biomed. Res. Int'l. Article 698256 (Year: 2014).*
Diaz, L. M., Steele, M. H., Guerra, A. B., Aubert, F. E., Sloop, G. D., Diaz, H. a., . . . Metzinger, S. E. (2004). The Role of Topically Administered FK506 (Tacrolimus) at the Time of Facial Nerve Repair Using Entubulation Neurorrhaphy in a Rabbit Model. Annals of Plastic Surgery, 52(4), 407-413. https://doi.org/10.1097/01.sap.0000107780.37285.6d.

(Continued)

*Primary Examiner* — Sean M Basquill
(74) *Attorney, Agent, or Firm* — Hill & Schumacher (57) ABSTRACT

The present disclosure provides delivery systems for delivering FK506 locally to damaged nerve sites. Particulate FK506 incorporated into a fibrin gel, with the amount of FK506 sufficient to give an FK506 release rate over at least 14 days of at least 5 micrograms per milliliter of the treated tissue per day has been shown to remarkably improve axon regeneration. The delivery systems include particulate FK506 having sizes between about 500 microns to about 1 millimeter encapsulated in a fibrin matrix, powdered FK506 encapsulated within electrospun films, powdered FK506 encapsulated within a cellulose matrix, and a flexible film of small intestinal submucosa having a plurality of solid islands located on one side thereof, with each island containing a preselected amount of FK506 and a polyester. The local application of FK506 via the local delivery system disclosed herein results in excellent nerve regeneration while preventing the toxicity of systemic FK506 that has prevented clinicians from using FK506 routinely for treating severe cases of peripheral nerve injuries. In addition to being used for treatment of damaged nerve sites, the present systems may be applied to other types of injuries, including but not limited to spinal cord Injuries, stroke, vascularized composite allotransplantation (VCA) and local applications during solid organ transplants.

19 Claims, 11 Drawing Sheets

(56) References Cited

OTHER PUBLICATIONS

Steiner, J., Connolly, M., & Valentine, H. (1997). Neurotrophic actions of nonimmunosuppressive analogues of immunosuppressive drugs FK506, rapamycin and cyclosporin A. Nat. Med., 3(4), 421-428.

Toll, E. C., Seifalian, A. M., & Birchall, M. A. (2011). The role of immunophilin ligands in nerve regeneration. Regenerative Medicine, 6(5), 635-652. https://doi.org/10.2217/rme.11.43.

Udina, E., Rodríguez, F. J., Verdú, E., Espejo, M., Gold, B. G., & Navarro, X. (2004). FK506 enhances regeneration of axons across long peripheral nerve gaps repaired with collagen guides seeded with allogeneic Schwann cells. Glia, 47 (2), 120-129. https://doi.org/10.1002/glia.20025.

Gordon, T., Sulaiman, O., & Boyd, J. G. (2003). Experimental strategies to promote functional recovery after peripheral nerve injuries. Journal of the Peripheral Nervous System, 8(4), 236-250. https://doi.org/10.1111/j.1085-9489.2003.03029.x.

Pratt, W. B. (1998). The hsp90-based chaperone system: involvement in signal transduction from a variety of hormone and growth factor receptors. Proceedings of the Society for Experimental Biology and Medicine. Society for Experimental Biology and Medicine (New York, N.Y.), 217(4), 420-434. https://doi.org/10.3181/00379727-217-44252.

Anonymous: "Gibaldi's Drug Delivery Systems in Pharmaceutical Care", 2007 XP002795386, p. 26.

International Search Report of the parent PCT application PCT/CA2017/050410, dated Aug. 17, 2017.

Tajdaran et al. "A Novel Polymeric Drug Delivery System for Localized and Sustained Release of Tacrolimus (FK506)", Biotechnol. Bioeng., 112(9), 2015, pp. 1948-1953.

Kuffler, "An Assessment of Current Techniques for Inducing Axon Regeneration and Neurological Recovery Following Peripheral Nerve Trauma", Prog. Neurobiol., 116, 2014, pp. 1-12.

Chan, et al. "Improving Peripheral Nerve Regeneration: From Molecular Mechanisms to Potential Therapeutic Targets", Exper. Neurol., 261, 2014, pp. 826-835.

* cited by examiner

SYSTEM FOR DELIVERY OF FK506 FOR ENHANCING NERVE REGENERATION

FIELD

The present disclosure relates to a drug delivery system and method of delivering the immunophilin, FK506 to damaged nerve sites.

BACKGROUND

There are many challenges to improving nerve regeneration and functional outcomes following peripheral nerve injuries, specifically for large nerve defects, especially those that are incurred close to the spinal cord, and in the frequent cases where surgical nerve repair is delayed. Systemically-administered FK506, a naturally occurring immunophilin that has been widely used since the 1980's as an immunosuppressant drug (Tacrolimus) for organ transplantation, was found to significantly enhance nerve regeneration in a rat model (Gold et al, 1994). While there was some interest in the following decade (Diaz et al., 2004; Steiner et al., 1997; Toll et al., 2011; Udina et al., 2004), the significant toxicity of systemic FK506 deterred further investigations. The drug is toxic to the kidney, there is an elevated risk of development of skin cancers, and the risk of opportunistic infections due to immunosuppression.

The enhanced regenerative effect of FK506 is mediated via a calcineurin-independent pathway that is distinct from the pathways that mediate immunosuppression. FK506 binds to the FK506 binding protein-52 that initiates downstream intracellular signaling cascades, the details of which presently remain largely unknown, but the binding ultimately results in increased neurite extension in vivo and increased numbers of neurons regenerating their axons after delayed nerve injury through proposed pathways such as the MAP and ERK (Gordon and Sulaiman, 2003; Pratt, 1998).

Providing a system and method of delivery of FK506 which avoids the above-noted deleterious side effects would be one of the first opportunities of using an agent to boost nerve regeneration after nerve injuries and surgical repair.

SUMMARY

The present disclosure provides delivery systems for local delivery of FK506 to the site of the nerve lesion with surgical intervention. Particulate FK506 incorporated into a fibrin gel, with the amount of FK506 sufficient to give an FK506 release rate over at least 14 days of at least 5 micrograms per milliliter of the treated tissue per day, has been shown to remarkably improve axon regeneration after a nerve transection and surgical repair in a rat. The improved results cannot be obtained with lower dosages i.e. less than 5 micrograms per milliliter of the treated tissue per day over 14 days.

The delivery systems include particulate FK506 having sizes between about 500 microns to about 1 millimeter incorporated within a fibrin matrix, powdered FK506 incorporated within electrospun films, powdered FK506 incorporated within a cellulose matrix, and a flexible film of small intestinal submucosa having a plurality of solid islands located on one side thereof, with each island containing a preselected amount of FK506 and a polyester. The local application of FK506 via the local delivery system disclosed herein results in excellent neuron regeneration while preventing the toxicity of systemic FK506 that has prevented clinicians from using FK506 routinely for treating cases of peripheral nerve injuries.

The released FK506 from the delivery system is only detectable within the injured nerve, dossal root ganglia (DRGs), the entire spinal cord, and the muscles surrounding the nerve repair site, decreasing in concentration over time. The highest FK506 tissue concentration is detected within the entire spinal cord. No FK506 is detected in plasma, brain, liver, and heart during the entire period of drug release, thus showing the utility of the present method.

An embodiment provides a method of producing a delivery vehicle for locally delivering FK506 to damaged nerve sites, comprising:

a) mixing particles of FK506 with thrombin, said particles of FK506, having a size in a range from about 500 microns to about 1 millimeter, to form a mixture and, in turn, to physically blending the mixture to form a first homogenous mixture;

b) within about 5 minutes of producing the first homogenous mixture, adding a substantially equal volume of fibrinogen, and physically blending the fibrinogen and the homogenous mixture to produce a second homogenous mixture; and c) transferring the second homogenous mixture onto an aseptic surface to allow cross-linking of the fibrinogen by the thrombin in a second homogenous mixture to produce a fibrin gel based delivery system with the fibrin containing the FK506; and wherein, the particles of FK506 are present in said fibrin gel in a sufficient amount to give a FK506 release rate over at least 14 days of at least 5 micrograms per milliliter of the treated tissue per day.

An embodiment disclosed herein provides a formulation for local application to damaged nerve sites in mammals, comprising:

particles of FK506 suspended in fibrin, said particles of FK506 having a size in a range from about 500 microns to about 1 millimeter;

wherein the particles of FK506 are present in said fibrin in a sufficient amount to give a FK506 release rate over at least 14 days of at least 5 micrograms per milliliter of the treated tissue per day.

Another embodiment provides a method of producing a delivery vehicle for locally delivering FK506 to damaged nerve sites, comprising:

a) dissolving a polyester in an organic solvent to form a first solution;

b) mixing FK506 into said first solution whereupon the FK506 dissolves to form a second solution;

c) transferring a number of droplets of pre-selected volumes of the second solution onto a surface of a flexible film of small intestinal submucosa (SIS); and d) allowing the organic solvent to evaporate over a period of time to leave behind a plurality of solid islands on the small intestinal submucosa, each island including the polyester and FK506, the number of droplets being selected so that, upon formation of the solid islands, the film of small intestinal submucosa remains flexible;

wherein the FK506 is present in said solid islands in a sufficient amount to give a FK506 release rate over at least 14 days of at least 5 micrograms per milliliter of the treated tissue per day.

Another embodiment disclosed herein provides a method of producing a delivery vehicle for locally delivering FK506 to damaged nerve sites, comprising:

a) dissolving a polyester in an organic solvent to form a first solution;

b) mixing FK506 into said first solution whereupon the FK506 dissolves to form a second solution;

c) transferring the second solution to a charged dispenser needle of an electrospinning apparatus and dispensing the second solution from the charged dispenser needle onto a grounded collector of the electrospinning apparatus to form an electrospun sheet; and d) separating the electrospun sheet from the grounded collector, wherein the FK506 is present in said electrospun sheet in a sufficient amount to give a FK506 release rate over at least 14 days of at least 5 micrograms per milliliter of the treated tissue per day.

The present disclosure also provides a drug delivery system for local application to target tissue sites in mammals, comprising: particulate FK506 having a size in a range from about 500 microns to about 1 millimeter;

and a delivery vehicle for locally delivering the FK506 to the target tissue sites, wherein the particulate FK506 is present in said delivery vehicle in an amount to release FK506 over at least 14 days.

In an embodiment the particulate FK506 is released at a rate of at least 5 micrograms per milliliter of the target tissue per day.

The drug delivery system is configured for physical contact with the target tissue site. The drug delivery system is for use as a wrap around the target issues in the central or peripheral nervous system. These target tissue sites comprise injured peripheral nerve tissues, injured spinal cord tissues, or stroke damaged tissues. The target tissue sites may comprise vascularized composite allografts or solid organ transplants. The delivery vehicle may comprise a fibrin matrix, wherein the fibrin matrix may be a fibrin gel formed by cross-linking of fibrinogen by thrombin.

A further understanding of the functional and advantageous aspects of the disclosure can be realized by reference to the following detailed description and drawings.

BRIEF DESCRIPTION OF THE DRAWINGS

The following is a description, by way of example only, of a method and system to improve axon regeneration after surgical repair of a severely injured nerve in accordance with the present disclosure, reference being had to the accompanying drawings, in which:

FIG. 2C shows the same after 28 days post drug delivery system implantation. FK506 was detectable within the proximal injured sciatic nerve, DRGs (L4, L5), the entire spinal cord, and the muscles surrounding the nerve repair site, decreasing in concentration over time. FK506 content within the tissues was determined using mass spectrometry. (Mean±standard deviation, n=4).

FIGS. 3A and 3B show that in vivo FK506 release from delivery systems containing particulate FK506 and FK506 microspheres double the number of regenerating neurons. The number of retrogradely labelled motor (FIG. 3A) and sensory neurons (FIG. 3B) that regenerated their axons 7 millimeters distal from the site of nerve transection and repair site three (3) weeks following drug delivery system treatment. Motor neurons in the spinal cord (FIG. 3A; 50 microns (μm) sections, all sections counted) and sensory neurons in the dorsal root ganglia (FIG. 3B; 20 μm sections, every fifth section counted) were labelled with a fluorescent dye to count the motor and sensory neurons that regenerated nerves past the injury and surgical repair site. When the injured nerve in the experimental group was treated with a fibrin gel loaded with either microspheres containing FK506 or particulated FK506, all the motor neurons regenerated their axons (the dashed line indicates the total number of motor neurons that send axons into the intact tibial nerve) and a significantly increased number of sensory neurons regenerated their axons as compared to when the nerves in the control group were treated with empty microspheres or no drug delivery system. Nerve regeneration did not increase significantly after treatment with solubilized FK506 within the fibrin gel. The group treated with empty microspheres and the no drug delivery system treatment group had similar numbers of neurons that regenerated their axons. Data (n=6) represent the mean±standard error of the mean. *p<0.05.

DETAILED DESCRIPTION

Various embodiments and aspects of the system and method of delivering FK506 to damaged nerve sites will be described with reference to details discussed below. The following description and drawings are illustrative of the disclosure and are not to be construed as limiting the disclosure. The Figures are not to scale. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions.

As used herein the term "hydrogel" means polymeric hydrophobic material with a structure that renders it capable of holding water in a three-dimensional network.

Several exemplary systems for local delivery of FK506 to nerve sites will be described followed by studies on one of the systems.

The inventors have discovered a formulation, that, when applied to damaged nerves in mammals, results in healing of the damaged nerves. This formulation includes particles of FK506 suspended in fibrin gel, said particles of FK506 having a size in a range from about 500 microns to about 1 millimeter. The particles of FK506 are present in the fibrin in a sufficient amount to give a FK506 release rate over at least 14 days of at least 5 micrograms per milliliter of the treated tissue per day.

An embodiment of a method of producing a delivery vehicle for locally delivering FK506 to damaged nerve sites includes mixing particles of FK506 with thrombin, with the particles of FK506 having a size in a range from about 500 microns to about 1 millimeter to form a mixture and physically blending the mixture to form a first homogenous mixture. Within about 5 minutes of producing the first homogenous mixture, a substantially equal volume of fibrinogen is added to the first homogenous mixture followed by physically blending the fibrinogen and the homogenous mixture to produce a second homogenous mixture. This second homogenous mixture is then transferred onto an aseptic surface in a clean environment to allow cross linking of the fibrinogen by the thrombin in the second homogenous mixture to produce a fibrin gel based delivery system containing the FK506.

The concentration of the thrombin is in a range from about 5 to about 500 International units (IU) per milliliter of calcium chloride, and the concentration of the fibrinogen is in a range from about 75 to about 115 milligrams per milliliter of aprotinin solution.

Such concentration ranges of thrombin and fibrinogen ensure that a) the elastic module of the developed delivery system matches that of the nervous tissue and the surrounding environment, b) the developed delivery system provides sustained release of FK506 over a 14-day period without any initial burst release. Thrombin and fibrinogen are not required to be present in the same amount. However, the more thrombin provided, higher cross-linking will occur in the final fibrin mesh and thus, a gel with higher density will be formed.

In an embodiment, the concentration of the thrombin is 5 International units (IU) per milliliter of water, and the concentration of the fibrinogen is in a range from about 75 to about 115 milligrams per milliliter of water.

Once this FK506 containing fibrin gel has been produced, it is applied to the injured site quickly prior to the gel dehydration. An example of an injured site is a peripheral nerve that has undergone damage and surgical repair. The studies described below show that the particles of FK506 need to be present in the fibrin gel in a sufficient amount to give a FK506 release rate over at least 14 days of at least 5 micrograms per milliliter of the treated tissue per day in order to obtain full nerve regeneration. Thus, a method of medical treatment of peripheral nerve damage includes physically contacting the fibrin gel containing this minimum amount of FK506 to an injured peripheral nerve site prior to closing the wound site containing the injured peripheral nerve site.

For applying the delivery system around the nerve injury site after microsurgical repair of the injured nerve, the developed hydrogel based delivery system can be easily manipulated with surgical forceps and be wrapped around the nerve, centering it at the repair site by placing one portion of the delivery system underneath and another portion on top of the repair site. The delivery system can be secured around the nerve by gently opposing the two portions on one another.

While the above treatment has been described with respect to peripheral nerve injuries, it will be understood that the present method may be applied to other types of injuries, including but not limited to spinal cord Injuries, stroke, vascularized composite allotransplantation (VCA) and local applications during solid organ transplants to mention a few non-limiting examples. Following stroke and spinal cord injury, epicortical implantation and intrathecal implantation of the delivery system, or other locations within the central nervous system can reduce the adverse effects associated with the immune system driven secondary injury. An FK506 delivery system also further enhances repair and regeneration through endogenous stem cell stimulation. In addition, the proposed delivery system represents an effective long-lasting immunosuppressive delivery system which addresses one of the main challenges in solid organ transplantation and VCA. By implanting the delivery system subcutaneously or at the location of the transplanted organ, a long term sustained dose of immunosuppressive can be achieved, which minimizes the chance of toxicity and severe side effects, while maximizes the graft survival following transplantation.

Other means of producing a delivery vehicle for locally delivering FK506 to damaged nerve sites includes dissolving a polyester in an organic solvent to form a first solution, mixing FK506 into the first solution whereupon the FK506 dissolves to form a second solution, transferring a plurality of droplets of pre-selected volumes of the second solution onto a surface of a flexible film of small intestinal submucosa, and allowing the organic solvent to evaporate over a period of time to leave behind a plurality of solid islands on the small intestinal submucosa. The number of the solid islands are selected so that upon formation of the solid islands on the submucosa, the film of small intestinal submucosa remains flexible so that it can be easily shaped to the wound site in question.

The polyester has a molecular weight in a range from about 5000 Daltons to about 13,000 Daltons. The polyester could be, but is not limited to, any one of poly(lactic-co-glycolic acid) (PLGA) and polycaprolactone. A preferred polyester is PLGA having a molecular in a range from about 5000 Daltons to about 13,000 Daltons.

Another method of producing a delivery vehicle for locally delivering FK506 to damaged nerve sites includes dissolving a polyester in an organic solvent to form a first solution, mixing FK506 into this first solution whereupon the FK506 dissolves to form a second solution. The second solution is transferred to a charged dispenser needle of an electrospinning apparatus and the second solution is dispensed from the charged dispenser needle onto a grounded collector of the electrospinning apparatus to form an electrospun sheet which when fully formed is separated from the grounded collector.

The electrospinning apparatus may be operated in a non-weaving mode to produce a non-woven electrospun sheet, or it may be operated in a weaving mode to produce a woven electrospun sheet. As noted in the method described above, the polyester has a molecular weight in a range from about 5000 Daltons to about 13,000 Daltons. The polyester is any one of poly(lactic-co-glycolic acid) (PLGA) and polycaprolactone. A preferred polyester is PLGA having a molecular weight in a range from about 5000 Daltons to about 13,000 Daltons.

While the two methods described above may be carried out in ambient conditions, room temperature and pressure, and standard humidity, these conditions may be varied. For example, the process is not restricted to room temperature. The dissolving steps may be carried out at lower temperatures down to 5° C. and at higher temperatures up to 30° C. However, the step of evaporation is preferably carried out room temperature.

Another embodiment of a method of producing a delivery vehicle for locally delivering FK506 to damaged nerve sites includes mixing cellulose or any derivative of cellulose, or any combination of the two, with water and particles of FK506, in which the particles of FK506 have a size in a range from about 500 microns to about 1 millimeter. The cellulose, water and particles of FK506 are physically mixed to form a homogenous mixture. The homogenous mixture is transferred onto an aseptic surface under clean conditions to allow cross linking of the any one or combination of cellulose and any derivative of cellulose to produce a hydrogel based delivery system containing the FK506. The hydrogel forms spontaneously, and does not require any cross linking agent.

The cellulose, or derivatives or any combination thereof is present in the water in a range from about 3% by weight, to about 15% by weight.

For nerves having a diameter of 1 to 2 millimeters, the minimum amount of FK506 release rate over at least 14 days of at least 5 micrograms per milliliter of the treated tissue per day is required. For nerves having a diameter larger than 2 millimeters, the FK506 release rate over at least 14 days should be greater than 5 micrograms per milliliter of the treated tissue per day.

The released FK506 from the delivery system placed at the site of sciatic nerve injury is only detectable within the injured nerve, dossal root ganglia (DRGs), the entire spinal cord, and the muscles surrounding the nerve repair site, decreasing in concentration over time. The highest FK506 tissue concentration is detected within the entire spinal cord. No FK506 is detected in plasma, brain, liver, and heart during the entire period of drug release.

EXAMPLES

The effect of a novel FK506 local delivery system on peripheral nerve regeneration following nerve transection and repair was investigated. In this drug delivery system, FK506 was incorporated in fibrin gel in solubilized, particulated, and poly(lactic-co-glycolic acid) (PLGA) microsphere encapsulated forms. Such drug delivery system localizes the FK506 around the nerve injury site and allows sustained FK506 release. In this study, we have shown we can (a) locally deliver FK506 to the site of a nerve injury in a rat model, (b) the locally delivered FK506 is transported from the site of nerve injury to the nervous system and is mainly accumulated within the spinal cord, and (c) this local delivery doubles the axon regeneration of motor and sensory neurons, an effect size that far exceeded our expectations. Combined with the fact that FK506 has had regulatory approval for years and is very inexpensive, we believe that local delivery of FK506 for nerve injuries can rapidly move into clinical trials following these animal studies.

Methods

Thirty adult female Sprague-Dawley rats were randomized into five groups (n=6). The experimental group included rats treated with fibrin gel loaded with FK506 by incorporating 10 microliters solubilized FK506 in acetonitrile (2 milligrams per milliliter), 200 micrograms solid FK506 particulates, or 5 milligrams of FK506 containing microspheres into the thrombin solution before it was mixed with fibrinogen to form a gel. Rats in the control groups either did not receive any delivery system treatment or received fibrin gel with empty microspheres (without any FK506).

During the procedure, the sciatic nerve was exposed and the main branches were dissected. The tibial (TIB) nerve was transected 5 millimeters distal to its bifurcation from the common peroneal (CP) nerve and sural nerves with fine microsurgical scissors. The proximal TIB nerve stump was cross-sutured to the distal stump of a cut CP nerve. In the groups receiving the fibrin gel based drug delivery system, the nerve suture site was surrounded by two 40 microliters of the fibrin gels (containing applicable components for each group) formed by pipetting the fluid fibrin mixture onto a Parafilm sheet as semi-rectangular drops (~5×5 millimeters) and placing the drops above and below the repair site. By gently opposing the drops, the delivery system was secured around the nerve. Three weeks after repair, the number of neurons that regenerated their axons were determined using retrograde labeling 7 millimeter distal to the repair site. Nerve samples at the location of retrograde labeling were collected for histomorphometric analysis. Using mass spectrometry, FK506 tissue concentrations were analyzed at the site of the injury, in sciatic nerve, dorsal root ganglia (DRGs), spinal cord, brain, heart, liver, kidney, and plasma at 7, 14, and 28 days post repair.

Results and Discussion

Figure 1A:
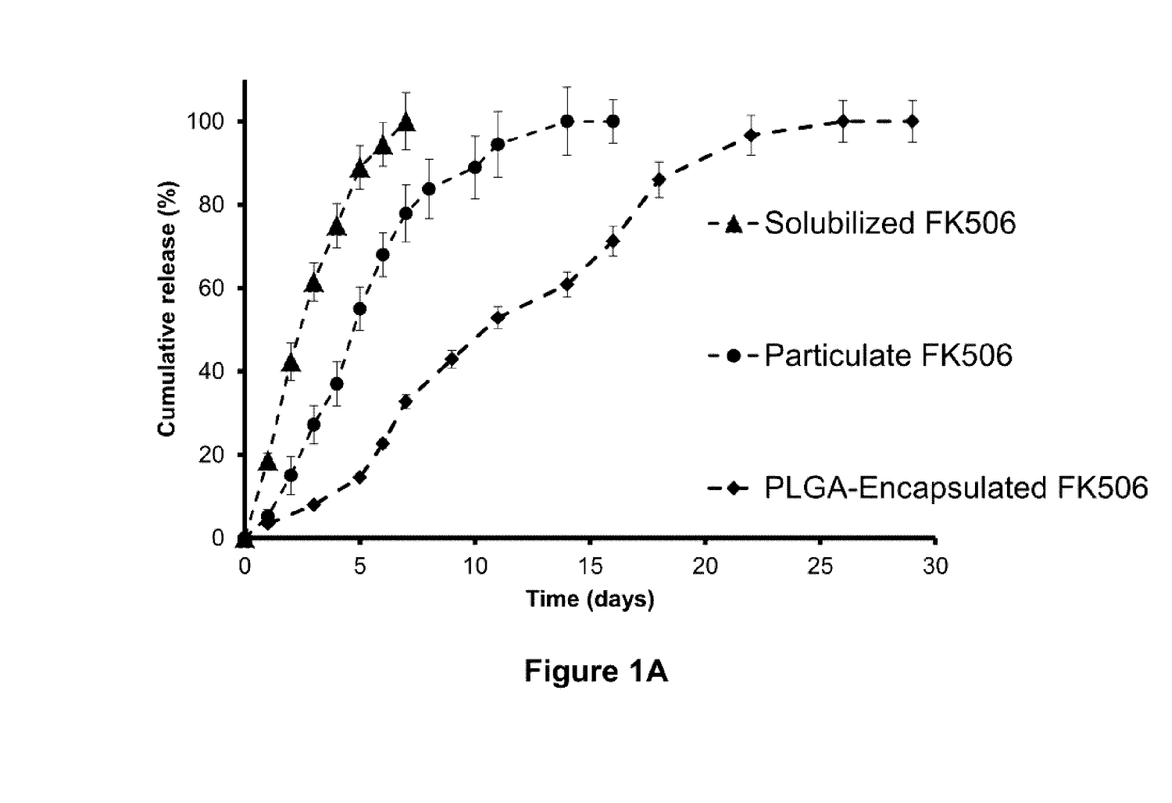
FIG. 1A shows in vitro FK506 release profile from fibrin gel and FIG. 1B shows in vivo FK506 release profile from fibrin gel for cumulative mass release of FK506 in solubilized (▲), particulate (●), and PLGA encapsulated (♦) forms from fibrin gel shows incorporation of solubilized FK506 into the gel provides release for up to only 5 days. Whereas, the FK506 release period gets extended to 14 days by incorporating particulate FK506 within the fibrin gel. The FK506 encapsulation in PLGA microspheres extends the sustained release to 28 days. (Mean±standard deviation, n=3 per release study)
Figure 1B:
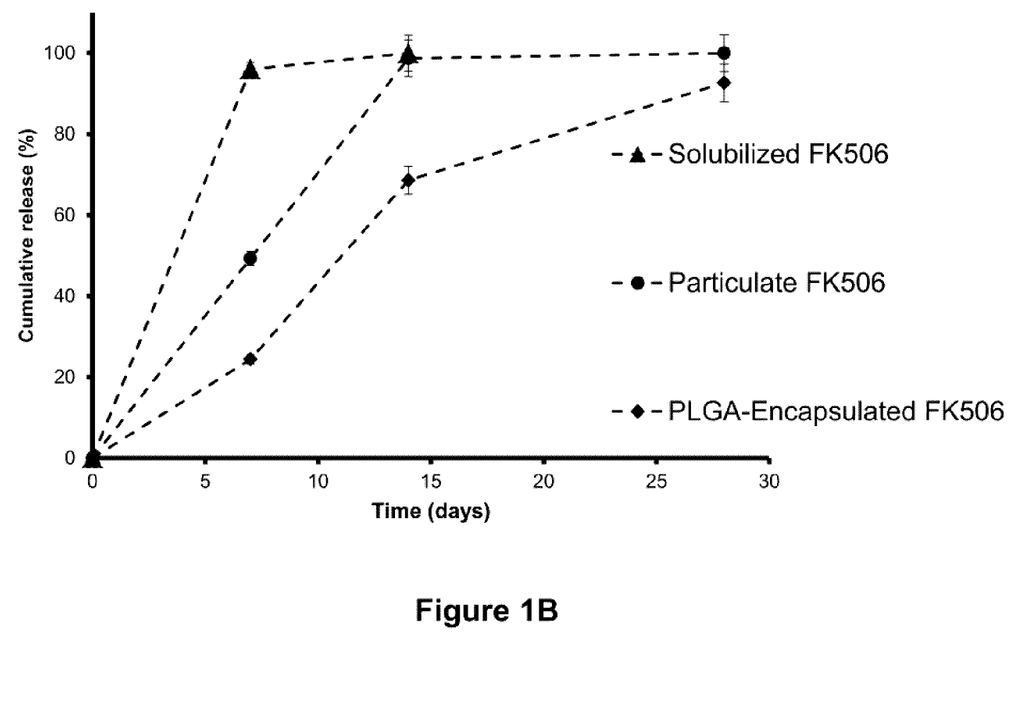

As shown in FIGS. 1A and 1B, solubilized FK506 was released from fibrin in 5 days both in vitro and in vivo respectively, thus giving the most rapid rate of release from the drug delivery system. The rate of release was slower when FK506 was dispersed in fibrin gel in particulate form. This form of drug incorporation provided sustained release of FK506 up to 14 days (FIGS. 1A and 1B). The longer release period was likely due to the lesser amount of FK506 that is available to be released from the gel matrix in the dissolved form at any given time. In another form of delivery system, FK506 was encapsulated within PLGA microspheres. Such FK506 incorporation within fibrin gel extended the drug release period to over 28 days (FIGS. 1A and 1B).

Figure 2A:
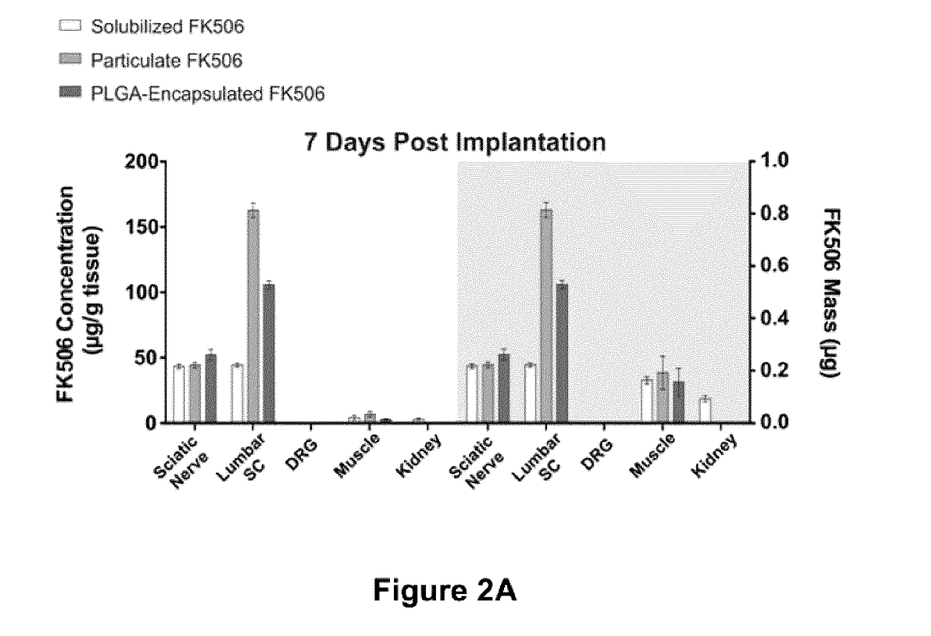
FIG. 2A shows organ exposure to the FK506 released from the drug delivery system after 7 days.
Figure 2B:
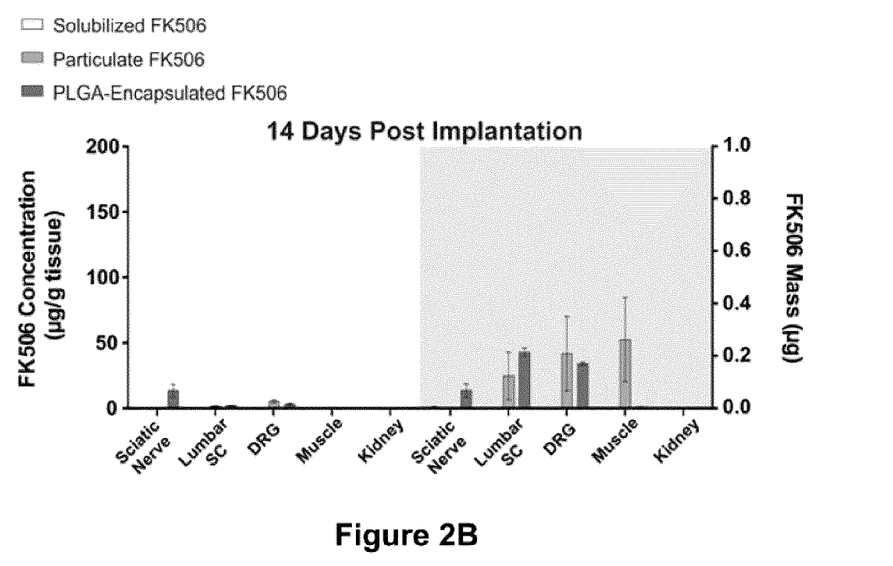
FIG. 2B shows the same after 14 days.
Figure 2C:
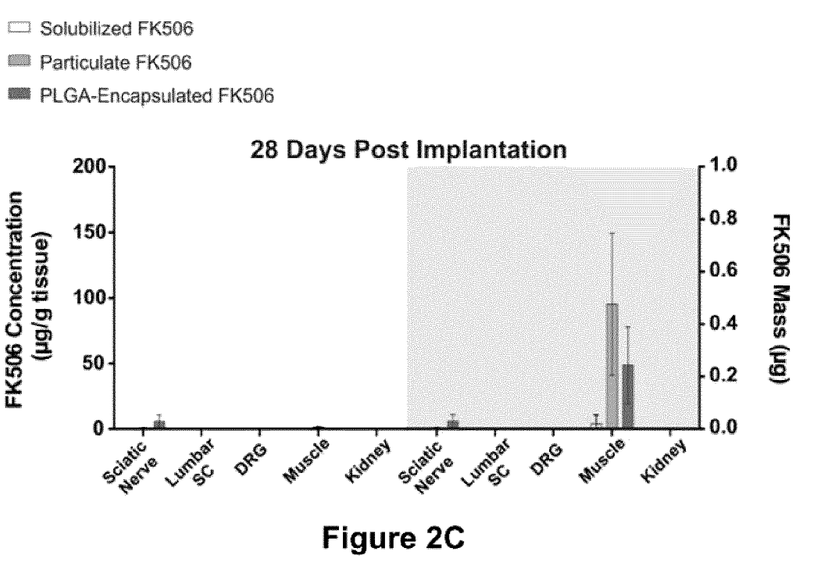

During the first week of drug release in vivo (FIG. 2A), FK506 was detected in the proximal injured sciatic nerve, the gluteal muscles surrounding the nerve, and at the highest level in the entire spinal cord. The concentration of FK506 was similar in the lumbar, thoracic, and cervical segments. Kidney tissues also had low FK506 levels only during the first week in the solubilized FK506 treated rats. These detected FK506 levels during the first week declined significantly to barely detectable levels at 14 days (FIG. 2B) and undetectable levels by 28 days (FIG. 2C). Within the DRGs (L4, L5), there was an accumulation of FK506 at 14 days, which was undetectable at 28 days. The contralateral sciatic nerve, contralateral gluteal muscles, and contralateral L4-L5 DRGs did not contain any FK506 during the entire period of the treatment. FK506 was not detectable, in the plasma, brain, liver, or heart during the entire study period.

Figure 3A:
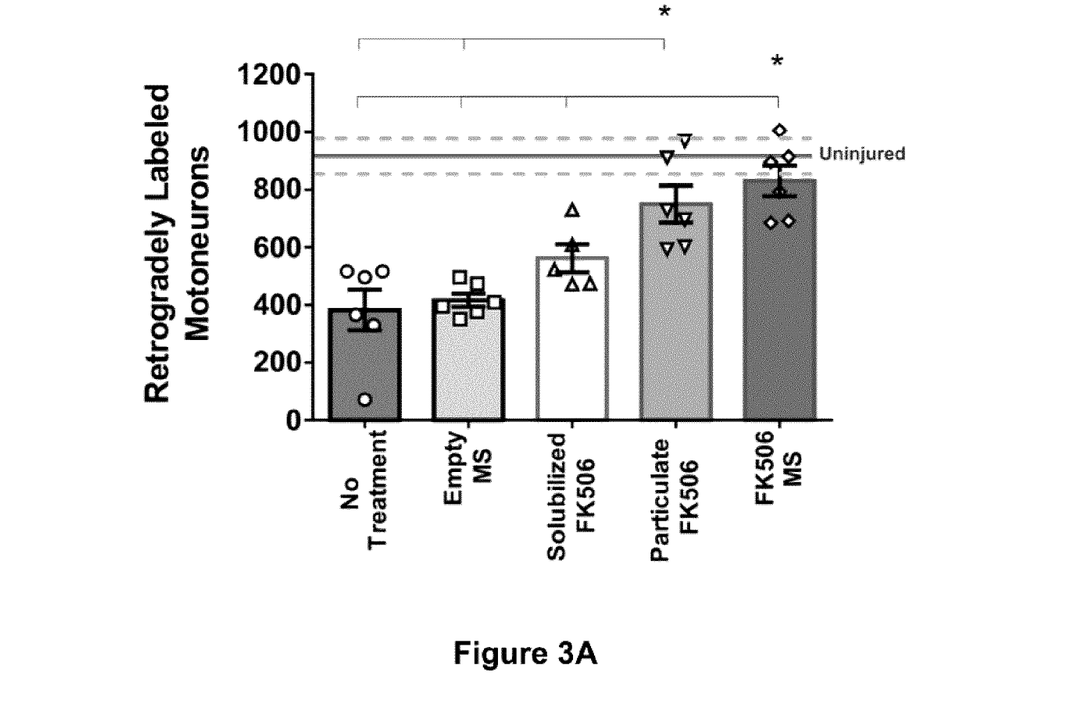
Figure 3B:
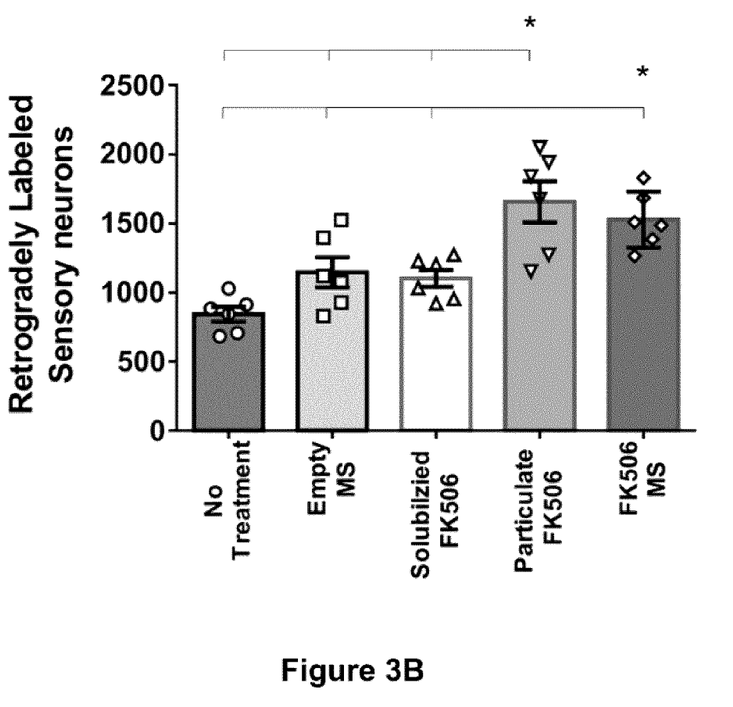
Figure 4A:
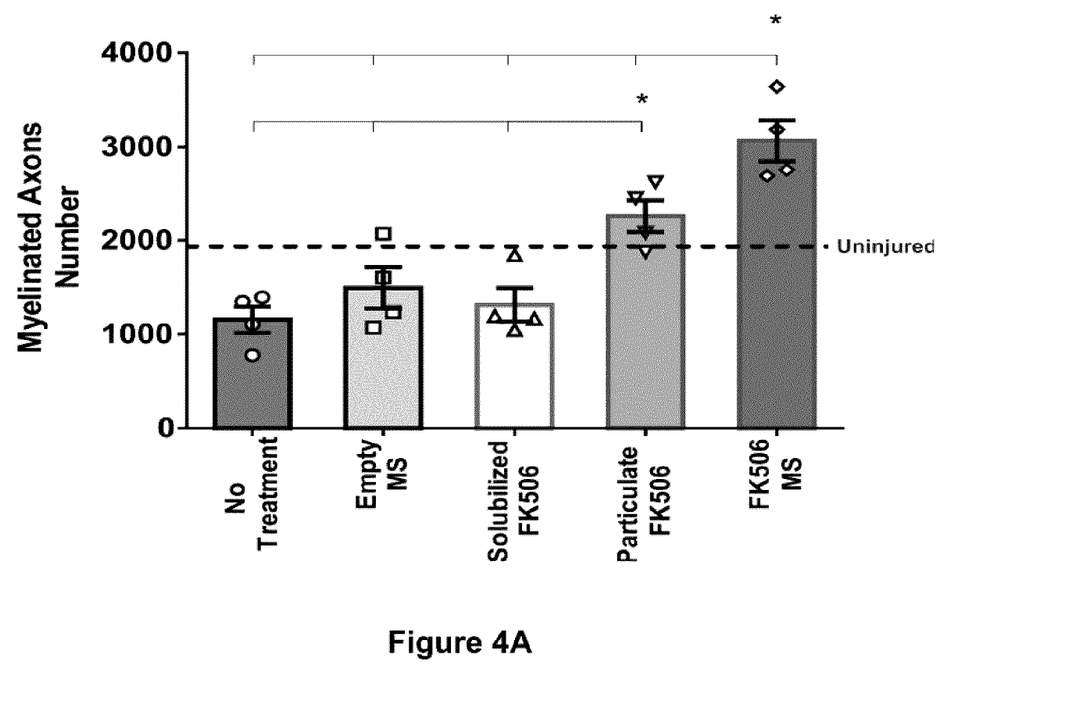
FIGS. 4A, 4B, 4C and 4D show histomorphometric analysis of the nerve cross-sections after treatment of nerve injury site with FK506 delivery system containing particulate FK506 and FK506 microspheres showing increased myelinated axon regeneration. Histomorphometric analysis of the nerve cross-sections indicated a significantly higher number of myelinated axons (FIG. 4A) in FK506 microspheres and particulate FK506 treated groups compared with the control groups. No groups exhibited significant differences in myelin thickness (FIG. 4B), fiber diameter (FIG. 4C), and G-ratio (FIG. 4D), but all were below the values of normal uninjured nerves (demonstrated by the horizontal dashed lines). Data represent the mean±standard error of the mean for 6 animals per group. *p<0.05.
Figure 4B:
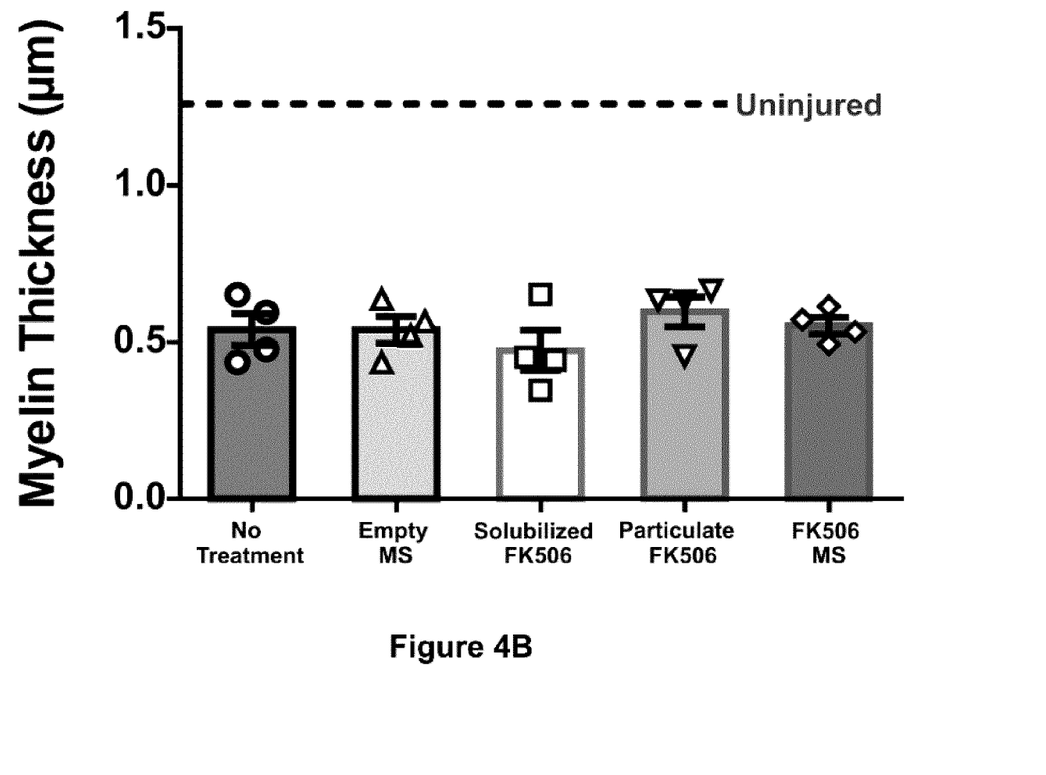
Figure 4C:
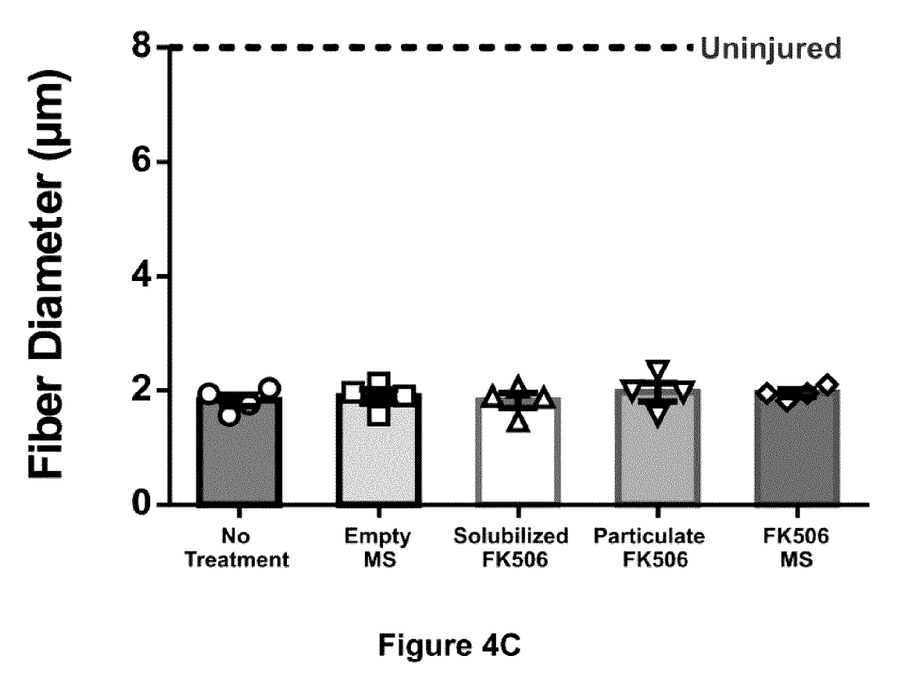
Figure 4D:
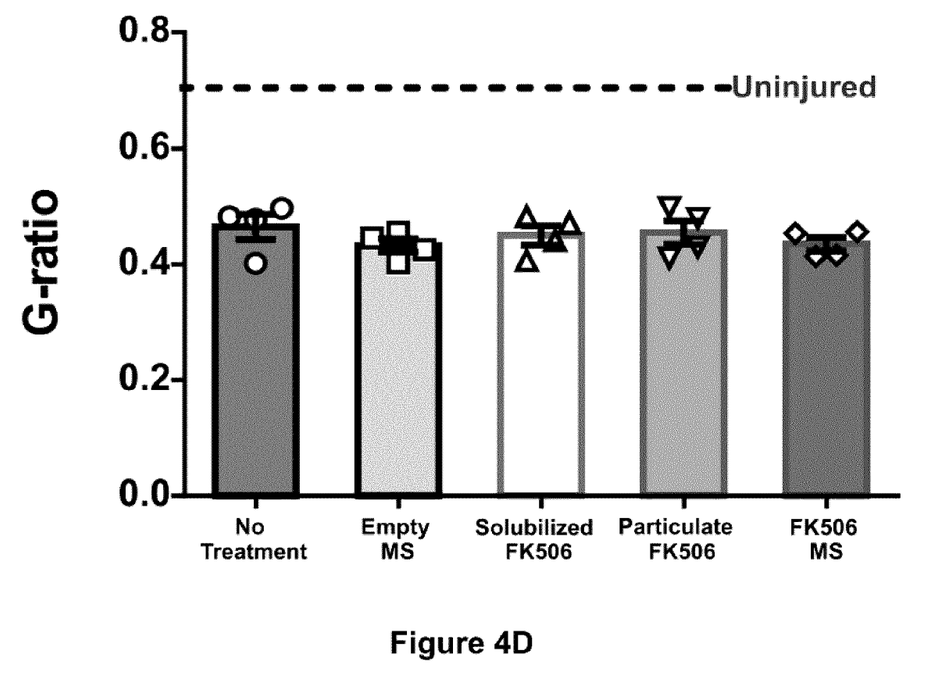

Following treating rats with FK506 containing local delivery systems, the systems having FK506-loaded microspheres and the particulate form of FK506 doubled the number of neurons regenerating their axons after injury. The number of the motor neurons that regenerated their axons for the FK506 microspheres treated group and the particulated FK506 treated group were significantly higher than the number in all the groups, including the solubilized FK506 and empty microspheres treated groups (FIG. 3A). The number of the sensory neurons that regenerated their axons was also significantly higher as compared with empty microspheres and solubilized FK506 (FIG. 3B). Treatment with FK506 microspheres allowed all the tibial motor neurons to regenerate their axons successfully. The empty MS and no treatment control groups of rats had similar numbers of injured neurons that regenerated their axons after transection and surgical repair. Histomorphometric analysis on the nerve cross-section demoinstrated increased numbers of myelinated axons following particulate FK506 and FK506 microspheres treatment. The number of myelinated axons for the particulate FK506, even though significantly higher than the control groups, was not statistically similar to the group in which the nerves were treated with FK506 microspheres (FIG. 4A). There were no significant differences in myelin thickness and fiber diameter in all the groups (FIG. 4B to 4C). The G-ratio, calculated as the ratio of the axon diameter to the total fiber diameter, was statistically equivalent for all groups (FIG. 4D).

Based on comparative studies by the inventors, it is noted that compared to the FK506 microsphere containing delivery system, the particulated FK506 containing delivery system is considered a more clinically suitable and commercially viable drug delivery system due to having a simpler synthesis process. Such a delivery system can be easily mass produced because it contains fewer inherent components than other systems we have developed. In addition, the final drug delivery system provides a much higher drug encapsulation efficiency, up to 10 times higher than the FK506 microsphere containing delivery system. Such higher drug encapusaltion efficiency is due to the direct incorporation of fresh FK506 drug within the fibrin gel of the delivery system, whereas, during the encapsulation process of the FK506 within the microspheres, up to 30 percent of the initial amount of FK506 can be lost. In addition, a main commercialization advantage of the particulated FK506 containing delivery system is having a higher weight percentage of the FK506 within the system compared to the FK506 microsphere containing delivery system. The particulated FK506 containing delivery system provides up to 100 times higher drug loading within the delivery system due to having a less amount of polymer compared to the FK506 microsphere containing delivery system.

CONCLUSION

The studies disclosed herein have demonstrated effective release of FK506 from poly(lactic-co-glycolic) acid (PLGA) microspheres and particulate FK506 while incorporated into a novel drug delivery system made of fibrin gel. The proposed drug delivery system has been shown to remarkably improve axon regeneration. The number of injured motor neurons that regenerated their axons was doubled in the groups treated with particulate FK506 containing delivery system and FK506 microspheres containing delivery system, allowing all the tibial motor neurons to regenerate their axons three weeks after nerve transection and surgical repair. FK506, in vivo, was found mainly at the nerve injury site, sciatic nerve, spinal cord, DRGs, and surrounding muscles, decreasing in concentration over time, with little to no drug detection in other vital organs. The highest accumulation of FK506 was found within the entire spinal cord. The local application of FK506 via the local delivery system disclosed herein results in excellent nerve regeneration while preventing the toxicity of systemic FK506 that has prevented clinicians from using FK506 routinely for treating severe cases of peripheral nerve injuries.

The foregoing description of the preferred embodiments of the disclosure has been presented to illustrate the principles of the disclosure and not to limit the disclosure to the particular embodiment illustrated. It is intended that the scope of the disclosure be defined by all of the embodiments encompassed within the following claims and their equivalents.

BIBLIOGRAPHY

Diaz, L. M., Steele, M. H., Guerra, A. B., Aubert, F. E., Sloop, G. D., Diaz, H. a., Metzinger, S. E. (2004). The Role of Topically Administered FK506 (Tacrolimus) at the Time of Facial Nerve Repair Using Entubulation Neurorrhaphy in a Rabbit Model. Annals of Plastic Surgery, 52(4), 407-413.

Gold, B., Storm-Dickerson, T., & Austin, D. (1994). The immunosuppressant FK506 increases functional recovery and nerve regeneration following peripheral nerve injury. Restor. Neurol. Neurosci., 6, 287-296.

Gordon, T., Sulaiman, O. & Boyd, J. G. (2003). Experimental strategies to promote functional recovery after peripheral nerve injuries. J. Peripher. Nerv. Syst, 8, 236-250.

Pratt, W. B. (1998). The hsp90-based chaperone system: involvement in signal transduction from a variety of hormone and growth factor receptors. Proceedings of the Society for Experimental Biology and Medicine. Society for Experimental Biology and Medicine (New York, N.Y.), 217(4), 420-434.

Steiner, J., Connolly, M., & Valentine, H. (1997). Neurotrophic actions of nonimmunosuppressive analogues of immunosuppressive drugs FK506, rapamycin and cyclosporin A. Nat. Med., 3(4), 421-428.

Toll, E. C., Seifalian, A. M., & Birchall, M. A. (2011). The role of immunophilin ligands in nerve regeneration. Regenerative Medicine, 6(5), 635-52.

Udina, E., Rodriguez, F. J., Verdú, E., Espejo, M., Gold, B. G., & Navarro, X. (2004). FK506 enhances regeneration of axons across long peripheral nerve gaps repaired with collagen guides seeded with allogeneic Schwann cells. Glia, 47(2), 120-9.

What is claimed is:

1. A drug delivery system for local application to target tissue sites in mammals, comprising:
    particulate FK506 having a size in a range from about 500 microns to about 1 millimeter; and
    a flexible film or sheet containing the particulate FK506 for locally delivering the particulate FK506 to the target tissue sites, said flexible film or sheet having dimensions selected for wrapping target nerve tissues in a central or peripheral nervous system in physical contact with the target nerve tissues,
    wherein a combination of a material the flexible wrap is made from and an amount of particulate FK506 present in said flexible film or sheet gives a release profile of the particulate FK506 over at least 14 days.

2. The drug delivery system according to claim 1, wherein the target tissue sites comprise injured peripheral nerve tissues, injured spinal cord tissues, or stroke damaged tissues.

3. The drug delivery system according to claim 1, wherein the target tissue sites comprise vascularized composite allografts or solid organ transplants.

4. The drug delivery system according to claim 1, wherein the flexible film or sheet comprises a fibrin matrix.

5. The drug delivery system according to claim 4, wherein the system is produced by a method comprising the steps of:
   a) mixing the particles of FK506 with thrombin to form a mixture and physically blending the mixture to form a first homogenous mixture;
   b) within about 5 minutes of producing the first homogenous mixture, adding a substantially equal volume of fibrinogen and physically blending the fibrinogen and the homogenous mixture to produce a second homogenous mixture; and
   c) transferring the second homogenous mixture onto an aseptic surface to allow cross-linking of the fibrinogen by the thrombin in second homogenous mixture in order to produce a fibrin gel-based delivery system with the fibrin containing the FK506.

6. The drug delivery system according to claim 5 wherein a concentration of the thrombin is in a range from about 5 to about 500 International units (IU) per milliliter of calcium chloride, and wherein a concentration of the fibrinogen is in a range from about 75 to about 115 milligrams per milliliter of aprotinin solution.

7. The drug delivery system according to claim 1, wherein the flexible film or sheet comprises a flexible film of small intestinal submucosa.

8. The drug delivery system according to claim 7, wherein the flexible film or sheet further comprises polyester dissolved in an organic solvent.

9. The drug delivery system according to claim 7, wherein the flexible film or sheet of small intestinal submucosa has a plurality of solid islands located on one side thereof, each island including the FK506 and the polyester.

10. The drug delivery system according to claim 1, wherein the flexible film or sheet comprises electrospun films.

11. The drug delivery system according to claim 10, wherein the system is produced by a method comprising the steps of:
    a) dissolving a polyester in an organic solvent to form a solution;
    b) mixing the particulate FK506 with said solution to form a mixture;
    c) transferring the mixture to a charged dispenser needle of an electrospinning apparatus and dispensing the mixture from the charged dispenser needle onto a grounded collector of the electrospinning apparatus to form an electrospun sheet; and
    d) separating the electrospun sheet from the grounded collector.

12. The drug delivery system according claim 1, wherein the flexible film or sheet comprises a cellulose matrix.

13. The drug delivery system according to claim 12, wherein the system is produced by a method comprising the steps of:
    a) mixing any one or combination of cellulose and any derivative of cellulose with water and the particles of FK506, and physically mixing the mixture to form a homogenous mixture; and
    b) transferring the homogenous mixture onto an aseptic surface to allow cross linking of the any one or combination of cellulose and any derivative of cellulose to produce a hydrogel-based delivery system containing the FK506.

14. A method of treatment of injured nerve tissue, comprising
    (a) wrapping the drug delivery system of claim 1 containing the FK506 around an injured nerve tissue in a wound site; and
    (b) closing the wound site.

15. The method according to claim 14 wherein the drug delivery system containing the FK506 is wrapped around the entire injured peripheral nerve.

16. The delivery vehicle according to claim 8 wherein the system is produced by a method comprising:
    a) dissolving the polyester in the organic solvent to form a solution;
    b) mixing the particulate FK506 into said solution to form a mixture;
    c) transferring a number of droplets of pre-selected volumes of the mixture onto a surface of a flexible film of small intestinal submucosa; and
    d) allowing the organic solvent to evaporate over a period of time to leave behind a plurality of solid islands on the small intestinal submucosa, each island including the polyester and FK506, the number of droplets being selected so that, upon formation of the solid islands, the film of small intestinal submucosa remains flexible;
    wherein the FK506 is present in the said solid islands in a sufficient amount to give a FK506 release rate over at least 14 days of at least 5 micrograms per milliliter of the treated tissue per day.

17. The delivery vehicle according to claim 16 wherein the polyester is any one of poly(lactic-co-glycolic acid) (PLGA) and polycaprolactone.

18. A method of treatment of an injured nerve tissue site, comprising
    wrapping the drug delivery system of claim 9 containing the flexible film of small intestinal submucosa around a damaged nerve tissue site with the solid islands contacting the injured nerve tissue site; and
    closing the wound site.

19. A method of treatment of injured nerve tissue, comprising
    wrapping the drug delivery system of claim 10 having a flexible electrospun film comprised of a preselected amount of FK506 around a damaged nerve tissue in a wound site; and
    closing the wound site,
    wherein the FK506 is present in said flexible electrospun film in a sufficient amount to give a FK506 release rate over at least 14 days of at least 5 micrograms per milliliter of the treated tissue per day.

* * * * *